US010351651B2

(12) United States Patent
Kobayashi et al.

(10) Patent No.: US 10,351,651 B2
(45) Date of Patent: Jul. 16, 2019

(54) IMPRINT MATERIAL CONTAINING SILSESQUIOXANE COMPOUND AND MODIFIED SILICONE COMPOUND

(71) Applicant: NISSAN CHEMICAL INDUSTRIES, LTD., Tokyo (JP)

(72) Inventors: Junpei Kobayashi, Funabashi (JP); Taku Kato, Funabashi (JP); Keisuke Shuto, Funabashi (JP); Masayoshi Suzuki, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 463 days.

(21) Appl. No.: 15/030,909

(22) PCT Filed: Oct. 6, 2014

(86) PCT No.: PCT/JP2014/076702
§ 371 (c)(1),
(2) Date: Apr. 21, 2016

(87) PCT Pub. No.: WO2015/064310
PCT Pub. Date: May 7, 2015

(65) Prior Publication Data
US 2016/0251469 A1    Sep. 1, 2016

(30) Foreign Application Priority Data
Oct. 30, 2013   (JP) .................................. 2013-225307

(51) Int. Cl.
*G03F 7/00*      (2006.01)
*C08F 290/06*    (2006.01)
*B32B 3/10*      (2006.01)
*G03F 7/027*     (2006.01)
*G03F 7/075*     (2006.01)
*C07F 7/08*      (2006.01)

(52) U.S. Cl.
CPC ............ *C08F 290/068* (2013.01); *B32B 3/10* (2013.01); *C07F 7/0838* (2013.01); *G03F 7/0002* (2013.01); *G03F 7/027* (2013.01); *G03F 7/0755* (2013.01); *G03F 7/0757* (2013.01); *Y10T 428/24802* (2015.01)

(58) Field of Classification Search
CPC ......... C08F 290/068; Y10T 428/24802; G03F 7/0002; G03F 7/027; G03F 7/0757; G03F 7/0755
See application file for complete search history.

(56) References Cited

U.S. PATENT DOCUMENTS

| 5,772,905 A | 6/1998 | Chou | |
|---|---|---|---|
| 2010/0244169 A1* | 9/2010 | Maeda | G02B 1/118 257/432 |
| 2013/0220533 A1* | 8/2013 | Tonegawa | B32B 38/10 156/247 |

FOREIGN PATENT DOCUMENTS

| JP | S64-23273 A | 1/1989 | |
|---|---|---|---|
| JP | 2004-212983 A | 7/2004 | |
| JP | 2008-105414 A | 5/2008 | |
| JP | 2008-202022 A | 9/2008 | |
| JP | 2009-259370 A | 11/2009 | |
| JP | 2010-013513 A | 1/2010 | |
| JP | 2012-099638 A | 5/2012 | |
| JP | 2013-065768 A | 4/2013 | |
| WO | 2011/049078 A1 | 4/2011 | |
| WO | WO-2012036209 A1 * | 3/2012 | ............ C09J 133/02 |
| WO | 2013/080741 A1 | 6/2013 | |

OTHER PUBLICATIONS

Machine translation of detailed description of JP 2012-099638 acquired Sep. 13, 2018.*
Hao et al., "Photocurable Silicon-Based Materials for Imprint Lithography," Proc. of SPIE, Emerging Lithographic Technologies XI, vol. 6517, Pt. 2, 2007, pp. 651729 1-9.
Palmieri et al., "Multi-level Step and Flash Imprint Lithography for Direct Patterning of Dielectrics," Proc. of SPIE, Emerging Lithographic Technologies X, vol. 6151, Pt. 1, 2006, pp. 61510J 1-9.
(Continued)

*Primary Examiner* — Gerard Higgins
(74) *Attorney, Agent, or Firm* — Oliff PLC

(57) ABSTRACT

A imprint material is provided, and a film that is prepared from the material and to which the pattern is transferred. An imprint material including: (A), (B), (C) and (D) components; a ratio of the amount of the (B) component to a total amount of the (A) component and the (B) component of 100% by mass is 5% by mass or more and 25% by mass or less: (A) a silsesquioxane compound having a repeating unit of Formula (1) and having two or more polymerizable groups of $X^0$ in Formula (1); (B) a silicone compound having a repeating unit of Formula (2) and having two polymerizable groups at ends thereof; (C) a photopolymerization initiator; and (D) a solvent $$\underset{k}{\underbrace{\left(\begin{array}{c}X^0\\|\\R^0\\|\\SiO_{1.5}\end{array}\right)}} \quad (1)$$

$$\left(\begin{array}{c}R^1\\|\\Si\\|\\R^2\end{array}\right)-O- \quad (2)$$

wherein the formulae, $R^1$ and $R^2$ are each independently a $C_{1-3}$ alkyl group; $R^0$ is a $C_{1-3}$ alkylene group; and k is an integer of 0 to 3.

12 Claims, No Drawings

(56) References Cited

OTHER PUBLICATIONS

Dec. 16, 2014 International Search Report issued in International Patent Application No. PCT/JP2014/076702.
May 3, 2016 International Preliminary Report on Patentability issued in International Patent Application No. PCT/JP2014/076702.
May 11, 2018 Office Action issued in Taiwanese Application No. 103136640.

* cited by examiner

IMPRINT MATERIAL CONTAINING SILSESQUIOXANE COMPOUND AND MODIFIED SILICONE COMPOUND

TECHNICAL FIELD

The present invention relates to an imprint material (a film forming composition for imprint) and a film that is formed from the material and to which a pattern is transferred. More specifically, the present invention relates to an imprint material that allows the film to which the pattern is transferred to be readily released from a mold at the time of mold release after curing and forms a cured film having heat resistance for a heating process at a temperature of higher than 200° C. and the film that is prepared from the material and to which the pattern is transferred.

BACKGROUND ART

In 1995, Professor Chou et al. of current Princeton University proposed a new technology called nano-imprint lithography (Patent Document 1). The nano-imprint lithography is a technology including bringing a mold having a certain pattern in contact with a substrate on which a resin film is formed, pressurizing the resin film, and using heat or light as external stimulus for curing to form a target pattern on the cured resin film. This nano-imprint lithography has advantages that nano-scale processing can be easily and inexpensively carried out as compared with photo-lithography in conventional semiconductor device production.

Therefore, in place of the photo-lithography, the nano-imprint lithography is a technology expected for applications in a semiconductor device, an opto-device, a display, a memory medium, and a bio-chip etc. Thus, various curable compositions for photo-nano-imprint lithography used for nano-imprint lithography have been described (Patent Document 2 and Patent Document 3). Furthermore, Patent Document 4 describes a photo-imprint material including a compound having a silicone framework and a light polymerization initiator.

When a costly mold is used in the nano-imprint lithography, longer operating life is required for the mold. However, at the time of mold release, when force required for peeling off the cured resin film from the mold, that is, a peeling force at the time of mold release (hereinafter, abbreviated as "mold release force" in this specification) is large, the resin is easily attached to the mold and thus the mold tends to become unusable. Therefore, the material used for nano-imprint lithography (hereinafter called an "imprint material" in this specification) should require a low mold release force property (a property that the cured resin film is easily peeled off from the mold). In device production, heating processes such as baking and soldering may be carried out. In some cases, the film is exposed to a high temperature of about 260° C. in the heating processes. At this time, if the film has low heat resistance and thus decomposed materials from the film are sublimed, inside of devices and apparatus and equipment for producing the device are contaminated. This causes serious problems. Further, depending on the type of the device, the device may be used in a place where the device is exposed to heat. In such a case, a similar problem may also arise and thus high heat resistance is required for a structure produced as an optical member in a product such as a solid state imaging device, a solar cell, an LED device, a display, and the like.

However, although various materials have ever been described as imprint materials, a material that satisfies both low mold release force and heat resistance of not causing the sublimation of the decomposed compounds at a temperature of more than 200° C., for example at 260° C., has not been reported.

PRIOR ART DOCUMENTS

Patent Documents

Patent Document 1: U.S. Pat. No. 5,772,905
Patent Document 2: Japanese Patent Application Publication No. 2008-105414 (JP 2008-105414 A)
Patent Document 3: Japanese Patent Application Publication No. 2008-202022 (JP 2008-202022 A)
Patent Document 4: Japanese Patent Application Publication No. 2013-065768 (JP 2013-065768 A)

SUMMARY OF THE INVENTION

Problem to be Solved by the Invention

The present invention is achieved based on the above described situations, and an object of the present invention is to provide an imprint material that allows a film to which a pattern is transferred to be readily released from a mold at the time of mold release after curing, that is, an imprint material that forms a film having a low mold release force property and forms a cured film having high heat resistance of not causing the sublimation of the decomposed compounds at a temperature exceeding 200° C., and to provide a film that is produced from the material and to which a pattern is transferred. Specifically, an object of the present invention is to provide a material that forms a cured film requiring a mold release force to a mold of more than 0 g/cm and 0.8 g/cm or less and the sublimation of the decomposed compounds at a temperature, for example 260° C., does not occur.

Means for Solving the Problem

As a result of intensive investigation for solving the above disadvantages, the inventors of the present invention have found that a composition including a silsesquioxane compound having two or more polymerizable groups and a silicone compound having two polymerizable groups at ends thereof, in which the ratio of the amount of the silicone compound having two polymerizable groups at ends thereof to the total amount of the silsesquioxane compound having two or more polymerizable groups and the silicone compound having two polymerizable groups at ends thereof of 100% by mass is 5% by mass or more and 25% by mass or less, the composition further including a light polymerization initiator and a solvent, is used as the imprint material. As a result, the inventors of the present invention have found that the use of the material significantly reduces the mold release force measured at the time of peeling off the cured film to which a pattern of the unevenness of the mold is transferred by photo-curing of the material on the surface of the mold having the unevenness from the surface of the mold having the unevenness and the film that is prepared from the material and to which the pattern is transferred does not cause the sublimation of the decomposed compounds even under a temperature of 260° C. Thus, the inventors of the present invention have accomplished the present invention.

Specifically, the present invention relates to, as a first aspect, an imprint material comprising:

(A) component;
(B) component;
(C) component, and
(D) component, in which
a ratio of the amount of the (B) component to a total amount of the (A) component and the (B) component of 100% by mass is 5% by mass or more and 25% by mass or less:

(A) a silsesquioxane compound having a repeating unit of Formula (1) and having two or more polymerizable groups of $X^0$ in Formula (1);

(B) a silicone compound having a repeating unit of Formula (2) and having two polymerizable groups at ends thereof;

(C) a photopolymerization initiator; and (D) a solvent

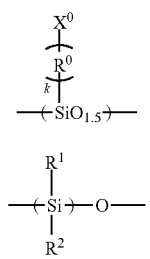

(in the formulae, $R^1$ and $R^2$ are each independently a $C_{1-3}$ alkyl group; $R^0$ is a $C_{1-3}$ alkylene group; and k is an integer of 0 to 3).

The present invention relates to, as a second aspect, the imprint material according to the first aspect, in which the (A) component is made of a complete cage structure and/or an incomplete cage structure, and a mixture of a random structure and a ladder structure.

The present invention relates to, as a third aspect, the imprint material according to the first aspect or the second aspect, further comprising a surfactant as an (E) component.

The present invention relates to, as a fourth aspect, the imprint material according to any one of the first aspect to the third aspect, in which the polymerizable groups in the (A) component and the (B) component are acryloyloxy groups, methacryloyloxy groups, vinyl groups, or allyl groups.

The present invention relates to, as a fifth aspect, a film to which a pattern is transferred, the film being formed from the imprint material according to any one of the first aspect to the fourth aspect.

The present invention relates to, as a sixth aspect, an optical member comprising the pattern-transferred film according to the fifth aspect provided on a substrate.

The present invention relates to, as a seventh aspect, a solid state imaging device comprising the pattern-transferred film according to the fifth aspect provided on a substrate.

The present invention relates to, as an eighth aspect, an LED device comprising the pattern-transferred film according to the fifth aspect provided on a substrate.

The present invention relates to, as a ninth aspect, a semiconductor device comprising the pattern-transferred film according to the fifth aspect provided on a substrate.

The present invention relates to, as a tenth aspect, a solar cell comprising the pattern-transferred film according to the fifth aspect provided on a substrate.

The present invention relates to, as an eleventh aspect, a display comprising the pattern-transferred film according to the fifth aspect provided on a substrate.

The present invention relates to, as a twelfth aspect, an electronic device comprising the pattern-transferred film according to the fifth aspect provided on a substrate.

Effects of the Invention

The cured film formed from the imprint material of the present invention has low mold release force property and does not show sublimation of the decomposed compounds even when the cured film is exposed at a temperature of, for example, 260° C.

The imprint material of the present invention can be cured by light and does not cause peeling of a part of the pattern at the time of releasing from the surface of the mold having unevenness. As a result, a film on which a desired pattern is precisely formed can be obtained. Therefore, the excellent pattern formation of photo-imprint can be achieved.

The film formed from the imprint material of the present invention can be formed onto any substrates. The pattern-transferred film formed after imprint can be suitably used for producing a member for which high transparency is required such as a solar cell, an LED device, and a display.

By changing the compounds and the content ratios of the compounds as the (A) component, the (B) component, and the (C) component, the curing rate and the dynamic viscosity of the imprint material of the present invention and the film thickness of the cured film formed from the imprint material of the present invention can be controlled. Therefore, a material corresponding to a device to be produced, an exposure process and a baking process can be designed with the imprint material of the present invention. This enables the process margin to be enlarged and thus the imprint material can be suitably used for production of optical members.

MODES FOR CARRYING OUT THE INVENTION

<(A) Component>

The silsesquioxane compound having two or more polymerizable groups as the (A) component is a compound having a main chain framework of a Si—O—Si bond, having the number of oxygen atoms of 1.5 in the repeating unit of Formula (1), and having two or more of the polymerizable groups of $X^0$ in the formula. Examples of the polymerizable groups may include acryloyloxy group, methacryloyloxy group, vinyl group, and allyl group. The acryloyloxy group may be called an acryloxy group and the methacryloyloxy group may be called a methacryloxy group. Examples of the $C_{1-3}$ alkylene group of $R^0$ in Formula (1) may include methylene group, ethylidene group [—CH(CH$_3$)— group], and propane-2,2-diyl group [—C(CH$_3$)$_2$— group].

The compound as the (A) component is commercially available and specific examples of the compound may include AC-SQ TA-100, MAC-SQ TM-100, AC-SQ SI-20, MAC-SQ SI-20, and MAC-SQ HDM (mentioned above are manufactured by Toagosei Co., Ltd.).

The compound as the (A) component can also be synthesized by using, for example, the compound of Formula (3) or the compound of Formula (4).

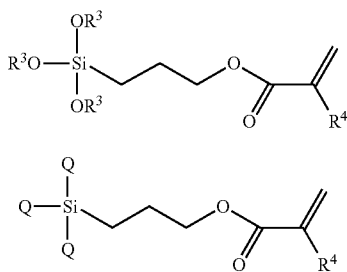

(in the formula, three $R^3$s are each independently a methyl group or an ethyl group; $R^4$ is a hydrogen atom or a methyl group; and three Qs are each independently a halogeno group).

Examples of the compound of Formula (3) may include 3-acryloyloxypropyltrimethoxysilane, 3-acryloyloxypropyl-triethoxysilane, 3-(trimethoxysilyl)propyl methacrylate, and 3-(triethoxysilyl)propyl methacrylate. Examples of the compound of Formula (4) may include 3-acryloyloxypropyl-trichlorosilane and 3-(trichlorosilyl)propyl methacrylate.

As the compound as the (A) component, a silsesquioxane compound having a weight average molecular weight of, for example, 700 to 7,000 can be used. Such a compound can be used singly or in combination of two or more of the compounds.

The (A) component in the imprint material of the present invention can provide heat resistance to the film after the pattern is transferred and can reduce the sublimation of the decomposed compounds under a temperature of more than 200° C., for example, a temperature of 260° C. By changing the type, the molecular weight, and the content ratio of the compound as the (A) component, the dynamic viscosity and the curing rate of the imprint material of the present invention and the film thickness of the cured film formed from the imprint material of the present invention can be controlled.

<(B) Component>

The silicone compound having two polymerizable groups at ends thereof as the (B) component is a compound having a silicone framework (siloxane framework) in the molecule and having two polymerizable groups at the ends of the molecule. Examples of the silicone framework may include a framework in which $R^1$ and $R^2$ are each independently a methyl group, an ethyl group, a propyl group, or an isopropyl group in Formula (2). In particular, a dimethylsilicone framework in which both $R^1$ and $R^2$ are methyl groups is preferable. Examples of the polymerizable groups may include acryloyloxy group, methacryloyloxy group, vinyl group, and allyl group. The acryloyloxy group may be called an acryloxy group and the methacryloyloxy group may be called a methacryloxy group.

The compound as the (B) component is commercially available and specific examples of the compound may include X-22-164, X-22-164AS, X-22-164A, X-22-164B, X-22-164C, X-22-164E, X-22-2445, and X-22-1602 (mentioned above are manufactured by Shin-Etsu Chemical Co., Ltd.).

The compound of the (B) component can be used singly or in combination of two or more of the compounds.

The ratio of the amount of the (B) component in the imprint material of the present invention to the total amount of the (A) component and the (B) component of 100% by mass is 5% by mass or more and 25% by mass or less. The ratio of less than 5% by mass results in an insufficient low mold release force property, whereas the ratio of more than 25% causes the sublimation of the decomposed compounds when the imprint material is exposed at a temperature of more than 200° C., for example, at a temperature of 260° C.

<(C) Component>

The photopolymerization initiator as the (C) component is not limited as long as photopolymerization initiators absorb light from the light source used at the time of photo-curing. Examples of the photopolymerization initiator may include organic peroxides such as tert-butylperoxy-iso-butyrate, 2,5-dimethyl-2,5-bis(benzoyldioxy)hexane, 1,4-bis[α-(tert-butyldioxy)-iso-propoxy]benzene, di-tert-butylperoxide, 2,5-dimethyl-2,5-bis(tert-butyldioxy)hexene hydroperoxide, α-(iso-propylphenyl)-iso-propyl hydroperoxide, tert-butyl hydroperoxide, 1,1-bis(tert-butyldioxy)-3,3,5-trimethylcy-clohexane, butyl-4,4-bis (tert-butyldioxy)valerate, cyclohexanone peroxide, 2,2',5,5'-tetra(tert-butylperoxycarbonyl) benzophenone, 3,3',4,4'-tetra(tert-butylperoxycarbonyl) benzophenone, 3,3',4,4'-tetra(tert-amylperoxycarbonyl) benzophenone, 3,3',4,4'-tetra(tert-hexylperoxycarbonyl) benzophenone, 3,3'-bis(tert-butylperoxycarbonyl)-4,4'-dicarboxybenzophenone, tert-butylperoxy benzoate, and di-tert-butyldiperoxy isophthalate; quinones such as 9,10-anthraquinone, 1-chloroanthraquinone, 2-chloroanthraquinone, octamethylanthraquinone, and 1,2-benzanthraquinone; benzoin derivatives such as benzoin methyl, benzoin ethyl ether, α-methylbenzoin, and α-phenylbenzoin; alkylphenone-based compounds such as 2,2-dimethoxy-1,2-diphenylethan-1-one, 1-hydroxy-cyclohexyl-phenyl-ketone, 2-hydroxy-2-methyl-1-phenyl-propan-1-one, 1-[4-(2-hydroxyethoxy)-phenyl]-2-hydroxy-2-methyl-1-propan-1-one, 2-hydroxy-1-[4-{4-(2-hydroxy-2-methyl-propionyl) benzyl}-phenyl]-2-methyl-propan-1-one, phenylglyoxylic acid methyl ester, 2-methyl-1-[4-(methylthio)phenyl]-2-morpholinopropan-1-one, 2-benzyl-2-dimethylamino-1-(4-morpholinophenyl)-1-butanone, and 2-dimethylamino-2-(4-methyl-benzyl)-1-(4-morpholin-4-yl-phenyl)-butan-1-one; acyl phosphine oxide-based compounds such as bis(2,4,6-trimethylbenzoyl)-phenylphosphine oxide and 2,4,6-trimethylbenzoyl-diphenyl-phosphine oxide; and oxime ester-based compounds such as 1-[4-(phenylthio)phenyl]-1,2-octanedione 2-(O-benzoyloxime), and 1-[9-ethyl-6-(2-methylbenzoyl)-9H-carbazol-3-yl]-ethanone O-acetyloxime.

The compound is commercially available and specific examples of the compound may include IRGACURE (registered trademark) 651, IRGACURE 184, IRGACURE 500, IRGACURE 2959, IRGACURE 127, IRGACURE 754, IRGACURE 907, IRGACURE 369, IRGACURE 379, IRGACURE 379EG, IRGACURE 819, IRGACURE 819DW, IRGACURE 1800, IRGACURE 1870, IRGACURE 784, IRGACURE OXE01, IRGACURE OXE02, IRGACURE 250, Darocur (registered trademark) 1173, Darocur MBF, Darocur 4265, Lucirin (registered trademark) TPO (mentioned above are manufactured by BASF Japan Ltd.), KAYACURE (registered trademark) DETX, KAYACURE MBP, KAYACURE DMBI, KAYACURE EPA, KAYACURE OA (mentioned above are manufactured by Nippon Kayaku Co., Ltd.), VICURE-10, VICURE 55 (mentioned above are manufactured by Stauffer Co. Ltd.), ESACURE (registered trademark) KIP150, ESACURE TZT, ESACURE 1001, ESACURE KTO46, ESACURE KB1, ESACURE KL200, ESACURE KS300, ESACURE EB3, Triazine-PMS, Triazine A, Triazine B (mentioned above are manufactured by Japan Siber-Hegner KK), ADEKA OPTOMER N-1717, ADEKA OPTOMER N-1414, and ADEKA OPTOMER N-1606 (manufactured by ADEKA CORPORATION).

The photopolymerization initiator as the (C) component can be used singly or in combination of two or more of the photopolymerization initiators.

The content of the (C) component in the imprint material of the present invention is preferably 0.1 phr to 30 phr and more preferably 1 phr to 20 phr with respect to the total mass of the (A) component and the (B) component. This is because the ratio of the content of the (C) component of less than 0.1 phr results in an insufficient curing property and thus deterioration in the patterning property occurs. The term "phr" in the specification means the mass of photopolymerization initiator to a total mass of the (A) component and the (B) component of 100 g.

<(D) Component>

The solvent as the (D) component in the present invention plays a role of adjusting viscosities of the silsesquioxane compound having two or more polymerizable groups as the compound (A) and a silicone compound having two polymerizable groups at ends thereof as the compound (B).

Examples of the solvent may include toluene, p-xylene, o-xylene, styrene, ethylene glycol dimethyl ether, propylene glycol monomethyl ether, ethylene glycol monomethyl ether, propylene glycol monoethyl ether, ethylene glycol monoethyl ether, ethylene glycol mono-isopropyl ether, ethylene glycol methyl ether acetate, propylene glycol monomethyl ether acetate, ethylene glycol ethyl ether acetate, diethylene glycol dimethyl ether, propylene glycol monobutyl ether, ethylene glycol monobutyl ether, diethylene glycol diethyl ether, dipropylene glycol monomethyl ether, diethylene glycol monomethyl ether, dipropylene glycol monoethyl ether, diethylene glycol monoethyl ether, triethylene glycol dimethyl ether, diethylene glycol monoethyl ether acetate, diethylene glycol, 1-octanol, ethylene glycol, hexylene glycol, diacetone alcohol, furfuryl alcohol, tetrahydrofurfuryl alcohol, propylene glycol, benzyl alcohol, 1,3-butanediol, 1,4-butanediol, 2,3-butanediol, γ-butyrolactone, acetone, methyl ethyl ketone, methyl isopropyl ketone, diethyl ketone, methyl isobutyl ketone, methyl n-butyl ketone, cyclohexanone, 2-heptanone, ethyl pyruvate, ethyl acetate, isopropyl acetate, n-propyl acetate, isobutyl acetate, n-butyl acetate, ethyl lactate, methanol, ethanol, isopropanol (2-propanol), tert-butanol, allyl alcohol, n-propanol, 2-methyl-2-butanol, isobutanol, n-butanol, 2-methyl-1-butanol, 1-pentanol, 2-methyl-1-pentanol, 2-ethylhexanol, trimethylene glycol, 1-methoxy-2-butanol, isopropyl ether, 1,4-dioxane, N,N-dimethylformamide, N,N-dimethylacetamide, N-methyl-2-pyrrolidone, 1,3-dimethyl-2-imidazolidinone, dimethyl sulfoxide, and N-cyclohexyl-2-pyrrolidine. The solvent is not particularly limited as long as the solvent can adjust the viscosities of the (A) component and the (B) component.

The solvent as the (D) component can be used singly or in combination of two or more of the solvents.

The solid content, which is defined as the content after removing the solvent as the (D) component from the total components containing the (A) component through the (C) component, an (E) component described below, and other additives described below, is preferably in an amount of 10% by mass to 90% by mass with respect to the amount of the imprint material of the present invention.

<(E) Component>

In the imprint material of the present invention, a surfactant may be included as the (E) component. The surfactant as the (E) component plays a role of adjusting a film forming property of the coating film to be obtained.

Examples of the surfactant may include a nonionic surfactant such as polyoxyethylene alkyl ethers including polyoxyethylene lauryl ether, polyoxyethylene stearyl ether, polyoxyethylene cetyl ether, and polyoxyethylene oleyl ether; polyoxyethylene alkylaryl ethers including polyoxyethylene octylphenyl ether and polyoxyethylene nonylphenyl ether; polyoxyethylene-polyoxypropylene block copolymers; sorbitan fatty acid esters including sorbitan monolaurate, sorbitan monopalmitate, sorbitan monostearate, sorbitan monooleate, sorbitan trioleate, and sorbitan tristearate; and polyoxyethylene sorbitan fatty acid esters including polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; a fluorochemical surfactant such as trade name Eftop (registered trademark) EF301, Eftop EF303, Eftop EF352 (manufactured by Mitsubishi Materials Electronic Chemicals Co., Ltd.), trade name MEGAFACE (registered trademark) F-553, MEGAFACE F-554, MEGAFACE F-556, MEGAFACE F-477, MEGAFACE F-171, MEGAFACE F-173, MEGAFACE R-08, MEGAFACE R-30, MEGAFACE R-30N (manufactured by DIC Corporation), Fluorad FC430, Fluorad FC431 (manufactured by Sumitomo 3M Ltd.), trade name Asahi guard (registered trademark) AG710, Surflon (registered trademark) S-382, Surflon SC101, Surflon SC102, Surflon SC103, Surflon SC104, Surflon SC105, Surflon SC106 (manufactured by Asahi Glass Co., Ltd.); and Organosiloxane Polymer KP341 (manufactured by Shin-Etsu Chemical Co., Ltd.).

The surfactant can be used singly or in combination of two or more of the surfactants. When the surfactant is used, the ratio thereof is preferably 0.01 phr to 40 phr and more preferably 0.01 phr to 10 phr with respect to the total mass of the (A) component, the (B) component, and the (C) component.

<Other Additive>

As long as the effect of the present invention is not impaired, the imprint material of the present invention can contain an epoxy compound, a photoacid generator, a photosensitizer, an ultraviolet absorber, an antioxidant, an adhesion promoting agent, or a mold release improver, if necessary.

Examples of the epoxy compound may include X-22-2046, X-22-343, X-22-2000, X-22-4741, X-22-163, X-22-163A, X-22-163B, X-22-163C, X-22-169AS, X-22-169B, X-22-173BX, X-22-173DX, X-22-9002, KF-102, KF-101, KF-1001, KF-1002, KF-1005, KF-105 (mentioned above are manufactured by Shin-Etsu Chemical Co., Ltd.), Epolead (registered trademark) GT-401, Epolead PB3600, Celloxide (registered trademark) 2021P, Celloxide 2000, Celloxide 3000, EHPE3150, EHPE3150CE, Cyclomer (registered trademark) M100 (mentioned above are manufactured by DAICEL CORPORATION), EPICLON (registered trademark) 840, EPICLON 840-S, EPICLON N-660, and EPICLON N-673-80M (mentioned above are manufactured by DIC Corporation).

Examples of the photoacid generator may include IRGACURE (registered trademark) PAG103, IRGACURE PAG108, IRGACURE PAG121, IRGACURE PAG203, IRGACURE CGI725 (mentioned above are manufactured by BASF Japan Ltd.), WPAG-145, WPAG-170, WPAG-199, WPAG-281, WPAG-336, WPAG-367 (mentioned above are manufactured by Wako Pure Chemical Industries, Ltd.), TFE Triazine, TME-Triazine, MP-Triazine, Dimethoxytriazine, TS-91, and TS-01 (SANWA CHEMICAL CO., LTD.).

Examples of the photosensitizer may include thioxanthene-based, xanthene-based, ketone-based, thiopyrylium salt-based, base styryl-based, merocyanine-based, 3-substituted coumarin-based, 3,4-substituted coumarin-based, cyanine-based, acridine-based, thiazine-based, phenothiazine-based, anthracene-based, coronene-based, benzanthracene-based, perylene-based, ketocoumarin-based, coumarin-based, and borate-based photosensitizers.

The photosensitizer can be used singly or in combination of two or more of the photosensitizers. The absorption wavelength in the UV region can be adjusted by using the photosensitizer.

Examples of the ultraviolet absorber may include TINUVIN (registered trademark) PS, TINUVIN 99-2, TINUVIN 109, TINUVIN 328, TINUVIN 384-2, TINUVIN 400, TINUVIN 405, TINUVIN 460, TINUVIN 477, TINUVIN 479, TINUVIN 900, TINUVIN 928, TINUVIN 1130, TINUVIN 111FDL, TINUVIN 123, TINUVIN 144, TINUVIN 152, TINUVIN 292, TINUVIN 5100, TINUVIN 400-DW, TINUVIN 477-DW, TINUVIN 99-DW, TINUVIN 123-DW, TINUVIN 5050, TINUVIN 5060, and TINUVIN 5151 (mentioned above are manufactured by BASF Japan Ltd.).

The ultraviolet absorber can be used singly or in combination of two or more of the ultraviolet absorbers. By using the ultraviolet absorber, the curing rate of the outmost surface of the film can be controlled at the time of photocuring and thus the mold release property may be improved.

Examples of the antioxidant may include IRGANOX (registered trademark) 1010, IRGANOX 1035, IRGANOX 1076, IRGANOX 1135, and IRGANOX 1520L (mentioned above are manufactured by BASF Japan Ltd.).

The antioxidant can be used singly or in combination of two or more of the antioxidants. By using the antioxidant, color change of the film into yellow caused by oxidation can be prevented.

Examples of the adhesion promoting agent may include 3-methacryloxypropyltrimethoxysilane and 3-acryloxypropyltrimethoxysilane. By using the adhesion promoting agent, the adhesion to the substrate is improved. The content of the adhesion promoting agent is preferably 5 phr to 50 phr and more preferably 10 phr to 50 phr with respect to the total mass of the (A) component and the (B) component.

Examples of the mold release improver may include a fluorine-containing compound. Examples of the fluorine-containing compound may include R-5410, R-1420, M-5410, M-1420, E-5444, E-7432, A-1430, and A-1630 (mentioned above are manufactured by DAIKIN INDUSTRIES, LTD.).

<Preparation of Imprint Material>

Although a method for preparing the imprint material of the present invention is not particularly limited as long as the method includes a step of mixing the (A) component, the (B) component, the (C) component, the (D) component, the (E) component as an optional component, and other additives if desired, so that the imprint material is in a homogeneous state.

The mixing order at the time of mixing the (A) component through the (E) component and optionally mixing the other additives does not matter as long as the homogeneous imprint material is obtained and is not particularly limited. Examples of the preparation method may include a method including a step of mixing the (B) component with the (A) component in a predetermined ratio. Examples of the method may also include the step of further mixing the (C) component, the (D) component, and the (E) component with the mixture to form the homogeneous imprint material. In the appropriate stage of the preparation method, a method including a step of further adding and mixing the other additives is included, if necessary.

<Photo-Imprint and Pattern-Transferred Film>

The imprint material of the present invention can provide a desired cured film by applying the imprint material onto a substrate and curing the coated film by light. Examples of coating methods may include publicly known or widely known methods such as a spin coating method, a dipping method, a flow coating method, an ink jet method, a spray method, a bar coating method, a gravure coating method, a slit coating method, a roll coating method, a transferring printing method, a brush coating, a blade coating method, and an air knife coating method.

Examples of the substrate to which the imprint material of the present invention is applied may include a substrate made from silicon wafer, glass on which an indium-tin oxide (ITO) film is formed (hereinafter abbreviated as "ITO substrate" in this specification), glass on which a silicon nitride (SiN) film is formed (SiN substrate), glass on which an indium-zinc oxide (IZO) film is formed, polyethylene terephthalate (PET), triacetyl cellulose (TAC), acryl, plastic, glass, quartz, and ceramic. Flexible substrates having flexibility can also be used. Examples of the flexible substrates may include triacetyl cellulose, polyethylene terephthalate, polymethyl methacrylate, a cyclo-olefin-(co)polymer, polyvinyl alcohol, polycarbonate, polystyrene, a polyimide, a polyamide, a polyolefin, polypropylene, polyethylene, polyethylene naphthalate, polyether sulfone, and a copolymer made from combination of these polymers.

Examples of the light source that is used to cure the imprint material of the present invention, which are not particularly limited, may include a high-pressure mercury lamp, low-pressure mercury lamp, an electrodeless lamp, a metal halide lamp, a KrF excimer laser, an ArF excimer laser, a $F_2$ excimer laser, electron beams (EB), and extreme ultraviolet (EUV). Generally, the wavelength of a G-line of 436 nm, an H-line of 405 nm, an I-line of 365 nm, or GHI mixed lines can be used. An exposure amount is preferably 30 mJ/cm$^2$ to 2,000 mJ/cm$^2$ and more preferably 30 mJ/cm$^2$ to 1,000 mJ/cm$^2$.

When the solvent as the (D) component is used, a baking step can be added in order to evaporate the solvent in at least one of the coated film before light irradiation or the cured film after light irradiation. Examples of the baking device, which is not particularly limited, may include devices that can bake the coating film using a hot plate, an oven, or a furnace under an adequate atmosphere, that is, in air or inert gas such as nitrogen or in vacuum. A baking temperature for evaporating the solvent is not particularly limited and the baking can be carried out, for example, at 40° C. to 200° C.

The device for carrying out the photo-imprint is not particularly limited as long as a target pattern can be obtained. Example of the device may include commercially available devices such as ST50 and ST50S-LED manufactured by TOSHIBA MACHINE CO., LTD., Sindre (registered trademark) 60 manufactured by OBDUCAT AB (publ), and NM-0801HB manufactured by MEISYO KIKO Co., Ltd. By using the device, a method for bonding the imprint material applied on the substrate to the mold by pressure and releasing it from the mold after photo-curing can be employed.

Examples of the mold material for the photo-imprint used in forming a film to which the pattern of the present invention is transferred may include quartz, silicon, nickel, alumina, carbonyl silane, glassy carbon, and polydimethyl silicone. However, the mold material is not particularly limited as long as the target pattern can be obtained. In order to improve the mold release property, mold release treatment in which the thin film of a fluorine-based compound or the like is formed on the surface of a mold may be carried out. Examples of a mold release agent used for the mold release treatment may include OPTOOL (registered trademark) HD and OPTOOL DSX manufactured by DAIKIN INDUSTRIES, LTD. However, the mold release agent is not particularly limited as long as the target pattern can be obtained.

The pattern size of the photo-imprint is in the nano-meter order and specifically the size is equivalent to a pattern size of less than 1 micron.

In the present invention, the 90° peeling test for evaluating the mold release force is a test in which generally, a bonding body (in the present invention, corresponding to the cured film formed from the imprint material) is bonded to a bonded body (in the present invention, corresponding to the film used as the substrate) and a resistance force (tensile force) generated at the time of peeling off the bonding body after predetermined time in a 90° direction at a predetermined peeling speed is measured. Usually, the measurement is carried out according to the evaluation method with reference to JIS Z0237. The value of the resistance force measured in this test is converted into the value per width of the bonding body, and the converted value can be evaluated as the mold release force.

In the test, the imprint material of the present invention is applied onto a film, the coating film on the film is bonded to the surface of a mold having unevenness, subsequently the coating film is photo-cured with the surface of the mold having unevenness bonding thereto, thereafter the cured film on the film is peeled off at 90° from the surface of the mold having unevenness, and thus, the mold release force is measured. The mold release force, that is, a value of a load when the cured film on the film is peeled off from the surface of the mold having unevenness is converted into a value per 1 cm of the width of the film. The converted value is preferably more than 0 g/cm and 0.8 g/cm or less. The smaller mold release force is more preferable in this range.

The film that is thus prepared from the imprint material of the present invention and to which a pattern is transferred, a semiconductor device including the film, and an optical member, a solid state imaging element, an LED device, a solar cell, a display, and an electronic device each of which includes the film on a substrate are also within the scope of the present invention.

EXAMPLES

Hereinafter, the present invention is further described in detail with reference to Examples and Comparative Examples. However, the present invention is not limited to these Examples.

The weight average molecular weight of the polymer described in Synthesis Example 1 described below is a measurement result by using gel permeation chromatography (hereinafter abbreviated as GPC in this specification). GPC system manufactured by SHIMADZU CORPORATION was used for the measurement. The configuration of the GPC system and measurement conditions are as follows:
  <GPC System Configuration>
  System controller: CBM-20A, Column oven: CTO-20, Auto sampler: SIL-10AF,
  Detector: SPD-20A and RID-10A, and Exhaust unit: DGU-20A3

GPC column: Shodex (registered trademark) KF-804L and KF-803L
  Column temperature: 40° C.
  Solvent: Tetrahydrofuran
  Flow rate: 1 mL/minute
  Standard sample: Six polystyrenes having different weight average molecular weights (197,000, 55,100, 12,800, 3,950, 1,260, and 580)

Synthesis Example 1

Into a 2,000 mL four-necked flask, 486.98 g of 3-acryloyloxypropyltrimethoxysilane and 400.53 g of methanol were charged and the mixture was cooled to 10° C. with stirring. To the mixture, a mixed solution of 112.23 g of 0.1N hydrochloric acid aqueous solution and 200.26 g of methanol was added dropwise over a period of 30 minutes at 10° C. to 25° C. Thereafter, the solution was stirred at room temperature for 1 hour and stirred with refluxing for 3 hours. The solution was concentrated under reduced pressure while adding 820 g of propylene glycol monomethyl ether acetate (hereinafter abbreviated as PGMEA in this specification) to the solution to replace the solution to a PGMEA solution and thus 600.0 g of the PGMEA solution of the silsesquioxane compound was obtained. To this PGMEA solution of the silsesquioxane compound, 120.0 g of propylene glycol monomethyl ether (hereinafter abbreviated as PGME in this specification) and the resultant mixture was heated at 40° C. for 2 hours to obtain the PGMEA/PGME solution of the silsesquioxane compound (PS-1). When the concentration of the solid content of the obtained PS-1 was measured at 150° C. with a halogen moisture analyzer (HR83-P, manufactured by METTLER TOLEDO Co., Ltd.), the concentration of the solid content was 50%. When the weight average molecular weight of the silsesquioxane compound obtained in this Synthesis Example 1 by GPC, the weight average molecular weight was 1,100. This silsesquioxane compound has the repeating unit of Formula (1). In the formula, $X^o$ is an acryloyloxy group; $R^o$ is a methylene group; and k is 3.

[Preparation of Imprint Material]

Example 1

9.5 g of AC-SQ TA-100 (manufactured by Toagosei Co., Ltd.) (hereinafter abbreviated as "AC-SQTA-100" in this specification), 0.5 g of X-22-1602 (manufactured by Shin-Etsu Chemical Co., Ltd.) (hereinafter abbreviated as "X-22-1602" in this specification), 0.25 g of Lucirin (registered trademark) TPO (manufactured by BASF Japan Ltd.) (hereinafter abbreviated as "Lucirin TPO" in this specification) (2.5 phr with respect to the total amount of AC-SQ TA-100 and X-22-1602), and 19 g of ethyl pyruvate were mixed to prepare an imprint material PNI-a1. In this Example, the ratio of the amount of the (B) component to the total amount of AC-SQ TA-100 corresponding to the (A) component and X-22-1602 corresponding to the (B) component of 100% by mass is 5% by mass.

Example 2

9 g of AC-SQ TA-100, 1 g of X-22-1602, 0.25 g of Lucirin TPO (2.5 phr with respect to the total amount of AC-SQ TA-100 and X-22-1602), and 19 g of ethyl pyruvate were mixed to prepare an imprint material PNI-a2. In this Example, the ratio of the amount of the (B) component to the total amount of AC-SQ TA-100 corresponding to the (A)

component and X-22-1602 corresponding to the (B) component of 100% by mass is 10% by mass.

Example 3

9 g of AC-SQ TA-100, 1 g of X-22-1602, 0.25 g of Lucirin TPO, 0.0051 g of MEGAFACE (registered trademark) R-30N (manufactured by DIC Corporation) (hereinafter abbreviated as "R-30N" in this specification) (0.05 phr with respect to the total amount of AC-SQ TA-100, X-22-1602, and Lucirin TPO), and 19 g of ethyl pyruvate were mixed to prepare an imprint material PNI-a3. In this Example, the ratio of the amount of the (B) component to the total amount of AC-SQ TA-100 corresponding to the (A) component and X-22-1602 corresponding to the (B) component of 100% by mass is 10% by mass.

Example 4

8 g of AC-SQ TA-100, 2 g of X-22-1602, 0.25 g of Lucirin TPO (2.5 phr with respect to the total amount of AC-SQ TA-100 and X-22-1602), and 19 g of ethyl pyruvate were mixed to prepare an imprint material PNI-a4. In this Example, the ratio of the amount of the (B) component to the total amount of AC-SQ TA-100 corresponding to the (A) component and X-22-1602 corresponding to the (B) component of 100% by mass is 20% by mass.

Example 5

8 g of AC-SQ TA-100, 2 g of X-22-1602, 0.25 g of Lucirin TPO (2.5 phr with respect to the total amount of AC-SQ TA-100 and X-22-1602), 0.0051 g of R-30N (0.05 phr with respect to the total amount of AC-SQ TA-100, X-22-1602, and Lucirin TPO), and 19 g of ethyl pyruvate were mixed to prepare an imprint material PNI-a5. In this Example, the ratio of the amount of the (B) component to the total amount of AC-SQ TA-100 corresponding to the (A) component and X-22-1602 corresponding to the (B) component of 100% by mass is 20% by mass.

Example 6

7.5 g of AC-SQ TA-100, 2.5 g of X-22-1602, 0.25 g of Lucirin TPO (2.5 phr with respect to the total amount of AC-SQ TA-100 and X-22-1602), and 19 g of ethyl pyruvate were mixed to prepare an imprint material PNI-a6. In this Example, the ratio of the amount of the (B) component to the total amount of AC-SQ TA-100 corresponding to the (A) component and X-22-1602 corresponding to the (B) component of 100% by mass is 25% by mass.

Example 7

9.5 g of PS-1 (solid content concentration 50% by mass) obtained in Synthesis Example 1, 0.25 g of X-22-1602, 0.125 g of Lucirin TPO (2.5 phr with respect to the total amount of the solid content after removing the solvent from PS-1 and X-22-1602), and 4.77 g of PGMEA were mixed to prepare an imprint material PNI-a7. In this Example, the ratio of the amount of the (B) component to the total amount of the solid content after removing the solvent from PS-1 corresponding to the (A) component and X-22-1602 corresponding to the (B) component of 100% by mass is 5% by mass.

Example 8

9 g of PS-1 obtained in Synthesis Example 1, 0.5 g of X-22-1602, 0.125 g of Lucirin TPO (2.5 phr with respect to the total amount of the solid content after removing the solvent from PS-1 and X-22-1602), and 5.02 g of PGMEA were mixed to prepare an imprint material PNI-a8. In this Example, the ratio of the amount of the (B) component to the total amount of the solid content after removing the solvent from PS-1 corresponding to the (A) component and X-22-1602 corresponding to the (B) component of 100% by mass is 10% by mass.

Example 9

9 g of PS-1 obtained in Synthesis Example 1, 0.5 g of X-22-1602, 0.125 g of Lucirin TPO (2.5 phr with respect to the total amount of the solid content after removing the solvent from PS-1 and X-22-1602), 0.0026 g of R-30N (0.05 phr with respect to the total amount of the solid content after removing the solvent from PS-1, X-22-1602, and Lucirin TPO) and 5.02 g of PGMEA were mixed to prepare an imprint material PNI-a9. In this Example, the ratio of the amount of the (B) component to the total amount of the solid content after removing the solvent from PS-1 corresponding to the (A) component and X-22-1602 corresponding to the (B) component of 100% by mass is 10% by mass.

Example 10

8 g of PS-1 obtained in Synthesis Example 1, 1 g of X-22-1602, 0.125 g of Lucirin TPO (2.5 phr with respect to the total amount of the solid content after removing the solvent from PS-1 and X-22-1602), and 5.52 g of PGMEA were mixed to prepare an imprint material PNI-a10. In this Example, the ratio of the amount of the (B) component to the total amount of the solid content after removing the solvent from PS-1 corresponding to the (A) component and X-22-1602 corresponding to the (B) component of 100% by mass is 20% by mass.

Example 11

8 g of PS-1 obtained in Synthesis Example 1, 1 g of X-22-1602, 0.125 g of Lucirin TPO (2.5 phr with respect to the total amount of the solid content after removing the solvent from PS-1 and X-22-1602), 0.0026 g of R-30N (0.05 phr with respect to the total amount of the solid content after removing the solvent from PS-1, X-22-1602, and Lucirin TPO), and 5.52 g of PGMEA were mixed to prepare an imprint material PNI-a11. In this Example, the ratio of the amount of the (B) component to the total amount of the solid content after removing the solvent from PS-1 corresponding to the (A) component and X-22-1602 corresponding to the (B) component of 100% by mass is 20% by mass.

Example 12

7.5 g of PS-1 obtained in Synthesis Example 1, 1.25 g of X-22-1602, 0.125 g of Lucirin TPO (2.5 phr with respect to the total amount of the solid content after removing the solvent from PS-1 and X-22-1602), and 5.77 g of PGMEA were mixed to prepare an imprint material PNI-a12. In this Example, the ratio of the amount of the (B) component to the total amount of the solid content after removing the solvent from PS-1 corresponding to the (A) component and X-22-1602 corresponding to the (B) component of 100% by mass is 25% by mass.

Comparative Example 1

10 g of AC-SQ TA-100, 0.25 g of Lucirin TPO (2.5 phr with respect to the amount of AC-SQ TA-100), and 19 g of ethyl pyruvate were mixed to prepare an imprint material PNI-b1. In this Comparative Example, the ratio of the amount of the (B) component is 0% by mass.

Comparative Example 2

7 g of AC-SQ TA-100, 3 g of X-22-1602, 0.25 g of Lucirin TPO (2.5 phr with respect to the total amount of AC-SQ TA-100 and X-22-1602), and 19 g of ethyl pyruvate were mixed to prepare an imprint material PNI-b2. In this Comparative Example, the ratio of the amount of the (B) component to the total amount of AC-SQ TA-100 corresponding to the (A) component and X-22-1602 corresponding to the (B) component of 100% by mass is 30% by mass.

Comparative Example 3

7 g of PS-1 obtained in Synthesis Example 1, 1.5 g of X-22-1602, 0.125 g of Lucirin TPO (2.5 phr with respect to the total amount of the solid content after removing the solvent from PS-1 and X-22-1602), and 6.02 g of PGMEA were mixed to prepare an imprint material PNI-b3. In this Comparative Example, the ratio of the amount of the (B) component to the total amount of the solid content after removing the solvent from PS-1 corresponding to the (A) component and X-22-1602 corresponding to the (B) component of 100% by mass is 30% by mass.

Comparative Example 4

10 g of X-22-1602, 0.25 g of Lucirin TPO, and 19 g of ethyl pyruvate were mixed to prepare an imprint material PNI-b4. In this Comparative Example, the ratio of the amount of the (B) component is 100% by mass.

[Photo-Imprint and Mold Release Force Test]

Each of the imprint materials obtained in Examples 1 to 12 and Comparative Examples 1 to 4 was applied onto a triacetyl cellulose film (FUJITAC (registered trademark) manufactured by FUJIFILM Corporation was used) (hereinafter abbreviated as "TAC film" in this specification) having a thickness of 80 μm using a bar coater (Full Automatic Film Applicator KT-AB3120, manufactured by COTEC CORPORATION). The solvent was removed by drying. Thereafter, the coating film on the TAC film was bonded to a moth-eye pattern mold by pressure using a roller. Subsequently, photo-curing of the coating film was carried out through a light exposure at 350 mJ/cm² from the TAC film side using an electrodeless uniform radiation device (QRE-4016A, manufactured by ORC MANUFACTURING CO., LTD.). With reference to JIS Z0237, the 90° peeling test was carried out to measure a load when the cured film formed on the TAC film (that is, the film to which the pattern was transferred) bonded to the surface of the mold having unevenness is completely peeled off from the surface of the mold having unevenness. A load per film width of 1 cm was calculated and the obtained value was determined to be the mold release force (g/cm). The results are listed in Table 1.

[Heat Resistance Evaluation]

Each of the imprint materials obtained in Examples 1 to 12 and Comparative Examples 1 to 4 was applied onto a non-alkali glass substrate by spin coating. Thereafter, a silicon wafer was bonded to the coating film on the non-alkali glass substrate and the bonded sample was placed in a nanoprinting device (NM-0801HB, manufactured by MEI-SYO KIKO Co., Ltd.). The sample was pressurized to 100 N over 10 seconds to remove babbles in the film and then was depressurized over 10 seconds. Thereafter, the sample was exposed to light at 350 mJ/cm² with the electrodeless uniform radiation device. The silicon wafer was peeled off to prepare a cured film having a thickness of 2 μm on the non-alkali glass substrate and the cured film was baked for 20 minutes on a hot plate kept at 260° C. Then, the presence or the absence of smoking at the time of baking was observed. The obtained results are listed in Table 1.

TABLE 1

|  | Mold release force (g/cm) | Smoking |
| --- | --- | --- |
| Example 1 | 0.71 | Absence |
| Example 2 | 0.61 | Absence |
| Example 3 | 0.65 | Absence |
| Example 4 | 0.60 | Absence |
| Example 5 | 0.58 | Absence |
| Example 6 | 0.52 | Absence |
| Example 7 | 0.8 | Absence |
| Example 8 | 0.76 | Absence |
| Example 9 | 0.74 | Absence |
| Example 10 | 0.65 | Absence |
| Example 11 | 0.64 | Absence |
| Example 12 | 0.6 | Absence |
| Comparative Example 1 | 2.20 | Absence |
| Comparative Example 2 | 0.5 | Presence |
| Comparative Example 3 | 0.67 | Presence |
| Comparative Example 4 | 0.31 | Presence |

From the results in Table 1, the following results were obtained. When the imprint materials obtained in Examples 1 to 12 were used, any of the imprint materials showed mold release forces of 0.8 g/cm or less. The obtained cured films showed no smoking at the time of baking and thus the sublimation of the decomposed compounds was not observed. In contrast, when the imprint materials obtained in Comparative Examples 1 to 4 were used, the mold release forces are far greater than 0.8 g/cm or the sublimation of the decomposed compounds was ascertained by observing the smoking at baking of the obtained cured films at a temperature of 260° C. As described above, the cured film obtained from the imprint material of the present invention requires a relatively low mold release force of 0.8 g/cm or less, and has excellent heat resistance.

INDUSTRIAL APPLICABILITY

The imprint material of the present invention can provide a cured film (a pattern-transferred film) formed from the imprint material of the present invention in which the cured film can be readily peeled off from a mold and has excellent heat resistance. Therefore, the cured film obtained from the imprint material can be suitably used for products such as a solar cell, an LED device, and a display.

The invention claimed is:

1. An imprint material consisting of:
(A) a silsesquioxane compound having a repeating unit of Formula (1) and having two or more polymerizable groups of $X^0$ in Formula (1);

where $R^0$ is a $C_{1-3}$ alkylene group, and k is an integer of 0 to 3;

(B) a silicone compound having a repeating unit of Formula (2) and having two polymerizable groups at ends thereof;

(2)

where $R^1$ and $R^2$ are each independently a $C_{1-3}$ alkyl group;

(C) a photopolymerization initiator;

(D) a solvent;

optionally (E) a surfactant; and optionally (F) an additive selected from the group consisting of a photoacid generator, a photosensitizer, an ultraviolet absorber, an antioxidant, an adhesion promoting agent, and a mold release improver, wherein a ratio of the amount of the (B) silicone compound to a total amount of the (A) silsesquioxane compound and the (B) silicone compound of 100% by mass is 5% by mass or more and 25% by mass or less.

2. The imprint material according to claim 1, wherein the (A) silsesquioxane compound is made of a complete cage structure, an incomplete cage structure, a complete cage structure and an incomplete cage structure, or a mixture of a random structure and a ladder structure.

3. The imprint material according to claim 1, wherein the (E) surfactant is present.

4. The imprint material according to claim 1, wherein the polymerizable groups in the (A) silsesquioxane compound and the (B) silicone compound are acryloyloxy groups, methacryloyloxy groups, vinyl groups, or allyl groups.

5. A film to which a pattern is transferred, the film being formed from the imprint material as claimed in claim 1.

6. An optical member comprising the film to which a pattern is transferred as claimed in claim 5 provided on a substrate.

7. A solid state imaging device comprising the film to which a pattern is transferred as claimed in claim 5 provided on a substrate.

8. An LED device comprising the film to which a pattern is transferred as claimed in claim 5 provided on a substrate.

9. A semiconductor device comprising the film to which a pattern is transferred as claimed in claim 5.

10. A solar cell comprising the film to which a pattern is transferred as claimed in claim 5 provided on a substrate.

11. A display comprising the film to which a pattern is transferred as claimed in claim 5 provided on a substrate.

12. An electronic device comprising the film to which a pattern is transferred as claimed in claim 5 provided on a substrate.

* * * * *